US011793779B2

(12) United States Patent
Sorsa et al.

(10) Patent No.: US 11,793,779 B2
(45) Date of Patent: Oct. 24, 2023

(54) HICA FOR USE IN PROPHYLAXIS AND/OR TREATMENT OF A DISEASE OR CONDITION INVOLVING DEGRADATION OF CARTILAGE AND/OR DISRUPTION OF CARTILAGE HOMEOSTASIS AND/OR INTEGRITY

(71) Applicant: Salarusta Oy, Espoo (FI)

(72) Inventors: Timo Sorsa, Helsinki (FI); Taina Tervahartiala, Vantaa (FI); Tuomo Karila, Vantaa (FI); Beniamin Cohen, Espoo (FI)

(73) Assignee: Salarusta Oy, Espoo (FI)

( * ) Notice: Subject to any disclaimer, the term of this patent is extended or adjusted under 35 U.S.C. 154(b) by 161 days.

(21) Appl. No.: 17/520,418

(22) Filed: Nov. 5, 2021

(65) Prior Publication Data

US 2022/0142956 A1     May 12, 2022

(30) Foreign Application Priority Data

Nov. 6, 2020   (FI) ..................................... 20206124

(51) Int. Cl.
     *A61K 31/19*      (2006.01)

(52) U.S. Cl.
     CPC ................................... *A61K 31/19* (2013.01)

(58) Field of Classification Search
     CPC ..................................................... A61K 31/19
     See application file for complete search history.

(56) References Cited

U.S. PATENT DOCUMENTS

| 9,631,029 | B2 | 4/2017 | Chiusaroli et al. | |
|---|---|---|---|---|
| 2004/0024024 | A1* | 2/2004 | Freskos ................ | C07D 401/12 514/513 |
| 2014/0056863 | A1* | 2/2014 | Greenberg ............ | A61K 36/06 424/94.1 |

FOREIGN PATENT DOCUMENTS

| WO | WO 97/00676 A1 | 1/1997 |
|---|---|---|
| WO | WO 99/65474 A2 | 12/1999 |
| WO | WO 2004/007024 A1 | 1/2004 |
| WO | WO 2018/200411 A1 | 11/2018 |

OTHER PUBLICATIONS

Alway, Stephen E. et al., "β-Hydroxy-β-methylbutrate (HMB) enhances the proliferation of satellite cells in fast muscles of aged rats during recovery from disuse atrophy," Experimental Gerontology, 48:973-984, (2013).
Anderson, Donald D. et al., "Post-Traumatic Osteoarthritis: Improved Understanding and Opportunities for Early Intervention," J. Orthop. Res. 29(6):802-809, (Jun. 2011).
Barreto, Goncalo et al., "Soluble biglycan: a potential mediator of cartilage degradation in osteoarthritis," Arthritis Research & Therapy, 17:379, (2015).
Berenbaum, F., "Osteoarthritis as an inflammatory disease (osteoarthritis is not osteoarthrosis!)," Osteoarthritis and Cartilage, 21:16-21, (2013).
Chockalingam, P.S. et al., "Elevated aggrecanase activity in a rat model of joint injury is attenuated by an aggrecanase specific inhibitor." Osteoarthritis and cartilage 19(3): 315-323, (2011).
Choi, Eun Young et al., "Del-1 is an endogenous inhibitor of leukocyte-endothelial adhesion limiting inflammatory cell recruitment," Science, 322(5904):1101-1104, (Nov. 14, 2008).
Chu, Q. et al., "Elevation of a collagenase generated type II collagen neoepitope and proteoglycan epitopes in synovial fluid following induction of joint instability in the dog," Osteoarthritis and Cartilage, 10:662-669, (2002).
Creamer, P. et al., "Osteoarthritis," Lancet, 350:503-08, (1997).
Deberg, Michelle et al., "New serum biochemical markers (Coll 2-1 and Coll 2-1 NO2) for studying oxidative-related type II collagen network degradation in patients with osteoarthritis and rheumatoid arthritis," Osteoarthritis and Cartilage, 13:258-265, (2005).
Dougados, M., "Evaluation of disease progression during nonsteroidal anti-inflammatory drug treatment: Imaging by arthroscopy," Osteoarthritis and Cartilage, 7:345-347, (1999).
Dougados, M., "The role of anti-inflammatory drugs in the treatment of osteoarthritis: a European viewpoint," Clin. Exp. Rheumatol., 19 (Suppl. 25):S9-S14, (2001).
Eskan, Mehmet A. et al., "The leukocyte integrin antagonist Del-1 inhibits IL-17-mediated inflammatory bone loss," Nat Immunol., 13(5):465-473, (Nov. 2012).
Felson, David T., "Priorities for osteoarthritis research: much to be done," Nature, 1-2, (2014).
Fex, E. et al., "Tissue-Derived Macromolecules and Markers of Inflammation in Serum in Early Rheumatoid Arthritis: Relationship to Development of Joint Destruction Hands and Feet," British Journal of Rheumatology, 36:1161-1165, (1997).
Flannery, Carl R. et al., "Expression of ADAMTS Homologues in Articular Cartilage," Biochemical and Biophysical Research Communications, 260:318-322, (1999).
Fosang, Amanda J. et al., "Degradation of cartilage aggrecan by collegnase-3 (MMP-13)," FEBS Letters, 380:17-20, (1996).
Garnero, Patrick et al., "Molecular Basis and Clinical Use of Biochemical Markers of Bone, Cartilage, and Synovium in Joint Diseases," Arthritis & Rheumatism, 43(5)953-968, (May 2000).
Georges, C. et al., "Serum biologic markers as predictors of disease progression in osteoarthritis of the knee," Letters, 590-591, (1997).
Glasson, Sonya S. et al., "Deletion of active ADAMTS5 prevents cartilage degradation in a murine model of osteoarthritis," Nature, 434:644-648, (Mar. 2005); Correction, 446:102, (Mar. 2007).

(Continued)

*Primary Examiner* — Nizal S Chandrakumar
(74) *Attorney, Agent, or Firm* — Alston & Bird LLP

(57) ABSTRACT

2-Hydroxy-isocaproic acid (HICA), or an ester or amide derivative, an enantiomer or a pharmaceutically acceptable salt thereof, for use in prevention and/or treatment of a disease or condition involving degradation of cartilage and/or disruption of cartilage homeostasis and/or integrity is disclosed.

9 Claims, 3 Drawing Sheets

(56) References Cited

OTHER PUBLICATIONS

Goldberg, Ronald L. et al., "Elevated Plasma Levels of Hyaluronate in Patients with Osteoarthritis and Rheumatoid Arthritis," Arthritis and Rheumatism, 34(7):799-807, (Jul. 1991).
Guilak, Farshid et al., "Osteoarthritis as a disease of the cartilage pericellular matrix," Matrix Biol, 71-72:40-50, (Oct. 2018).
Hajishengallis, George et al., "DEL-1-regulated immune plasticity and inflammatory disorders," Trends Mol. Med., 25(5):444-459, (2019).
Hanemaaijer, Roeland et al., "A Novel and Simple Immunocapture Assay for Determination of Gelatinase-B (MMP-9) Activities in Biological Fluids: Saliva for Patients with Sjögren's Syndrome Contain Increased latent and Active Gelatinase-B Levels," Matrix Biology, 17:657-665, (1998).
Honorati, M.C. et al., "Contribution of interleukin 17 to human cartilage degradation and synovial inflammation in osteoarthritis," Osteoarthritis and Cartilage, 10:799-807, (2002).
Hou, Wu-Shiun et al., "Cathepsin K is a critical protease in synovial fibroblast-mediated collagen degradation," American Journal of Pathology, 159(6):2167-2177, (Dec. 2001).
Huang, Zhengping et al., "Current status and future prospects for disease modification in osteoarthritis," Rheumatology, 57:iv108-iv123, (2018).
Hunter, David J. et al., "Cartilage markers and their association with cartilage loss on magnetic resonance imaging in knee osteoarthritis: the Boston Osteoarthritis Knee Study," Arthritis Research & Therapy, 9:R108, (2007).
Jahn, Sabrina et al., "Lubrication of articular cartilage," Physics Today, 4:48-54, (2018).
Karsdal, Morten A. et al., "Cartilage degradation is fully reversible in the presence of aggrecanase but not matrix metalloproteinase activity," Arthritis Research & Therapy, 10:R63, (2008).
Kojima, Toshihisa et al., "Early Degradation of Type IX and Type II Collagen with the Onset of Experimental Inflammatory Arthritis," Arthritis & Rheumatism, 44(1):120-127, (Jan. 2001).
Kreuger, Richard C. et al., "Chick Cartilage Chondroitin Sulfate Proteoglycan Core Protein," The Journal of Biological Chemistry, 265(20):12075-12087, (1990).
Lang, Charles H. et al., "Chronic α-hydroxyisocaproic acid treatment improves muscle recovery after immobilization-induced atrophy," Am J. Physiol Endocrinol. Metab., 305:E416- 428, (2013).
Larsson, S. et al., "An ARGS-aggrecan assay for analysis in blood and synovial fluid," Osteoarthritis and Cartilage, 22:242-249, (2014).
Malemud, Charles J., "Inhibition of MMPS and ADAM/ADAMTS," Biochem Pharmacol, 165:33-34, (Jul. 2019).
Malemud, Charles J., "Pharmacologic Interventions for preventing Chondrocyte Apoptosis in Rheumatoid Arthritis and Osteoarthritis," Drug Discovery—Concepts to Market, Chapter 4, 77-97, (2018).
Malfait, A.-M. et al., "the "Elusive DMOAD": Aggrecanase inhibition from laboratory to clinic," Clin Exp. Rheumatol, 37(Suppl. 120):S130-S134, (2019).
Manicourt, D. H. et al., "Oral salmon calcitonin reduces Lequesne's algofunctional index scores and decreases urinary and serum levels of biomarkers of joint metabolism in knee osteoarthritis," Arthritis Rheum 54(10): 3205-3211, (2006).
Martel-Pelletier, J. et al., Mellatoprotease and their modulation as treatment in osteoarthritis, Totowa, NJ: Humana Press, (2000).
Mazieres, B. et al., "Molecular markers of cartilage breakdown and synovitis at baseline as (predictors of structural progression of hip osteoarthritis. The ECHODIAH Cohort," Ann Rheum Dis 65(3): 354-359, (2005).
Mohan, V. et al., "Matrix Matrix metalloproteinase protein inhibitors: highlighting a new beginning for metalloproteinases in medicine," Metalloproteinases in Medicine 3: 31, (2016).
Mullan, R.H. et al., "Early changes in serum type II collagen biomarkers predict radiographic progression at one year in inflammatory arthritis patients after biologic therapy," Arthritis Rheum 56(9): 2919-2928, (2007).

Nagase, H. et al., "Aggrecanases and cartilage matrix degradation," Arthritis Res Ther 5(2): 94, (2003).
Nishizaki, K. et al., "Effect of Supplementation with a Combination of β-Hydroxy β- Metyhlbutyrae, L-Arginine, and L-Glutamine on Quadriceps Muscle Strength in Patients with Osteoarthritis Following Total Knee Arthroplasty," Clinical Nutrition, 33:S125-126, (2014).
Pelletier, J.P. et al., "Osteoarthritis, an inflammatory disease: potential implication for the selection of new therapeutic targets," Arthritis Rheum 44(6): 1237-1247, (2001).
Pelletier, J.P. et al., Etiopathogenesis of osteoarthritis. Baltimore, Lippincott Williams & Wilkins, (2000).
Roach, H. et al., "Association between the abnormal expression of matrix-degrading enzymes by human osteoarthritic chondrocytes and demethylation of specific CpG sites in the promoter regions," Arthritis Rheum 52(10): 3110-3124, (2005).
Schminke, B., S. et al., "Interleukin 17 inhibits progenitor cells in rheumatoid arthritis (cartilage," Eur J Immunol 46(2): 440-445, (2016).
Sharif, M. et al. "Serum hyaluronic acid level as a predictor of disease progression in osteoarthritis of the knee," Arthritis Rheum 38(6): 760-767, (1995).
Shin, J. et al., "Expression and function of the homeostatic molecule Del-1 in endothelial cells and the periodontal tissue," Clinical and developmental immunology, (2013).
Shiomi, T. et al., "Matrix metalloproteinases, a disintegrin and metalloproteinases, and a disintegrin and metalloproteinases with thrombospondin motifs in non-neoplastic diseases," Pathol Int 60(7): 477-496, (2010).
Singh, P. et al., "Phenotypic instability of chondrocytes in osteoarthritis: on a path to hypertrophy," Annals of the New York Academy of Sciences 1442(1): 17-34, (2019).
Sorsa, T. et al., "Activation of type IV procollagenases by human tumor-associated trypsin-2," Journal of Biological Chemistry 272(34): 21067-21074, (1997).
Tervahartiala, T. et al., "Proteolytic enzymes as indicators of periodontal health in gingival crevicular fluid of patients with Sjogren's syndrome," Eur J Oral Sci 103(1): 11-16, (1995).
Troeberg, L. et al., "Proteases involved in cartilage matrix degradation in osteoarthritis," Biochim Biophys Acta 1824(1): 133-145, (2012).
Verstappen, S.M. et al., "Radiographic joint damage in rheumatoid arthritis is associated with differences in cartilage turnover and can be predicted by serum biomarkers: an evaluation from 1 to 4 years after diagnosis," Arthritis Res Ther 8(1): R31, (2006).
Vilen, S.- T. et al., "Fluctuating roles of matrix metalloproteinase-9 in oral squamous cell carcinoma." The Scientific World Journal, (2013).
Vincenti, M.P. et al., "Transcriptional regulation of collagenase (MMP-1, MMP-13) genes in arthritis: integration of complex signaling pathways for the recruitment of gene-specific transcription factors," Arthritis Res 4(3): 157-164, (2002).
Wang, M. et al., "MMP13 is a critical target gene during the progression of osteoarthritis," Arthritis Res Ther 15(1): R5, (2013).
Wang, Z. et al., "DEL1 protects against chondrocyte apoptosis through integrin binding," J Surg Res. 231:1-9, (May 2018).
Wang, Z. et al., "Del1 Knockout Mice Developed More Severe Osteoarthritis Associated with Increased Susceptibility of Chondrocytes to Apoptosis," PLoS One 11(8): e0160684, (2016).
Wells, A.F. et al., "Correlation between increased hyaluronan localized in arthritic synovium and the presence of proliferating cells. A role for macrophage-derived factors," Arthritis Rheum 35(4): 391-396, (1992).
Yoshihara, Y. et al., "Matrix metalloproteinases and tissue inhibitors of metalloproteinases in synovial fluids from patients with rheumatoid arthritis or osteoarthritis," Ann Rheum Dis 59(6): 455-461, (2000).
WIPO Application No. PCT/FI2021/050750, PCT International Search Report dated Feb. 4, 2022.
Akhtar, Nahid et al., "Effect of a Herbal-Leucine mix on the IL-1β-induced cartilage degradation and inflammatory gene expression in human Chrondrocytes," BMC Complementary and Alternative Medicine, 11:66, (2011).

(56) References Cited

OTHER PUBLICATIONS

Nieminen, M.T. et al., "DL-2-Hydroxyisocaproic Acid Attenuates Inflammatory Responses in a Murine *Candida albicans* Biofilm Model," Clinical and Vaccine Immunology, 21(9):1240-1245, (2014).
Finnish Search Report for Finnish Patent Application No. 20206124 dated Feb. 9, 2021.

* cited by examiner

HICA FOR USE IN PROPHYLAXIS AND/OR TREATMENT OF A DISEASE OR CONDITION INVOLVING DEGRADATION OF CARTILAGE AND/OR DISRUPTION OF CARTILAGE HOMEOSTASIS AND/OR INTEGRITY

This application claims priority to FI application Serial No. 20206124, filed Nov. 6, 2020, which is incorporated herein by reference in its entirety and for all purposes.

TECHNICAL FIELD

The present disclosure relates to 2-hydroxyisocaproic acid (HICA) for use in prophylaxis and/or treatment of a disease or condition involving degradation of cartilage and/or disruption of cartilage homeostasis and/or integrity.

BACKGROUND

Osteoarthritis (OA) is the most prevalent joint disorder, resulting in degradation of articular cartilage, subchondral bone remodelling and varying degrees of synovial inflammation. The common type of arthritis is osteoarthritis which is degenerative joint disease. It is a common chronic, progressive musculoskeletal disorder characterized by gradual and partial loss of articular cartilage. OA and related degenerative and/or inflammatory joint disease can be defined as a heterogeneous group of conditions characterized by a combination of joint symptoms and signs stemming from defects in the articular cartilage in any joint and changes in the adjacent tissues, such as bone, synovial membrane, joint capsule, muscles, and ligaments thereof.

The ends of the articulating bones are covered with a 1- to 4-mm-thick layer of smooth, whitish tissue, the articular cartilage. It is hypocellular, avascular, aneural, and alymphatic tissue. It is essentially a water-filled network of collagen fibers permeated by highly charged macromolecules and other molecules. Water makes up about 70% of cartilage tissue by volume (Jahn and Klein 2018). Articular cartilage is an avascular tissue of which chondrocytes are the main cellular component. The matrix of hyaline articular cartilage is comprised primarily of collagen, proteoglycans and water molecules (Guilak, Nims et al. 2018). The chondrocytes in normal articular cartilage occupy approximately 5% of the tissue volume, while the extra-cellular matrix (ECM) makes up the remaining 95% of the tissue. The type II collagen which is the most abundant collagen protein in cartilage ECM has a role of framework providing tensite strength to articular cartilage. The most abundant proteoglycan is aggrecan which is composed of chondroitin sulphate and keratan sulphate binding to the linear core protein hyaluronic acid backbone (Guilak, Nims et al. 2018). Aggrecan provides cartilage with its compressibility and collagen provides its elasticity (Malfait and Tortorella 2019). One of the functional roles of cartilage in the joint is to allow bones to articulate on each other smoothly. Loss of articular cartilage, therefore, causes the bones to rub against each other leading to pain and loss of mobility, and is the hallmark of various diseases, among which rheumatoid arthritis (RA) and OA are the most prominent. A loss of articular cartilage may result in subchondral bone remodelling and pain.

Cartilage degeneration, a hallmark of OA, has its onset in mechanical injuries of the joint cartilage. Although trauma may be the first causal event in OA, the host inflammatory response may play an role in the pathogenesis arthritis and inflammation may be a driver to symptomatic OA (Berenbaum 2013, Felson 2014).

Pathophysiology

OA is not simply a mechanical "wear and tear" disease, but rather a condition in which well-defined biochemically mediated pathways bring about articular cartilage damage (Malfait and Tortorella 2019). The process leading to clinical OA may be triggered by some form of trauma resulting in inflammation with release of inflammatory mediators and matrix degrading enzymes into the articular space (Anderson, Chubinskaya et al. 2011). It may result from altered biomechanical stress that leads to alterations in chondrocyte metabolism (Karsdal, Madsen et al. 2008). Development of OA is multifactorial with significant influence from environmental factors. Alterations in cartilage may be the events leading to the onset of this pathology, and are followed by synovial inflammation and subchondral bone damage (Honorati, Bovara et al. 2002). Patients with OA may develop synovial disease in addition to cartilage degeneration (Dougados 2001).

In OA and RA, degradation of the ECM exceeds its synthesis, resulting in a net decrease in the amount of cartilage matrix or even in the complete erosion of the cartilage overlying the bone at the joint surface. The loss of aggrecan may be considered an early event of arthritis, occurring initially at the joint surface and progressing to the deeper zones. This is followed by degradation of collagen fibrils and mechanical failure of the tissue (Nagase and Kashiwagi 2003). The proteoglycans under physiological conditions may be more remodelled than collagens. Studies on cartilage explants suggest that collagen degradation occurs only after aggrecan is lost from the tissue, and that the presence of aggrecan protects the collagen from degradation. Furthermore, while aggrecan loss can be reversed, collagen degradation is irreversible, and cartilage cannot be repaired once collagen is lost. (Troeberg and Nagase 2012) In other words, once matrix metalloproteinases(MMP)mediated degradation was in progress, the capacity for repair was completely lost with regard to collagen type II synthesis, whereas proteoglycan synthesis was strongly attenuated. In contrast, at the time of maximal aggrecanase activity, the proteoglycan loss was fully reversible. In vivo studies indicate that aggrecan loss was reversible as long as the progression was not too advanced (Karsdal, Madsen et al. 2008). MMP-13 cleaves aggrecan in the interglobular domain IGD at the same site (Fosang, Last et al. 1996).

Collagenase and aggrecanase as proteolytic enzymes may play an role of the degradation process of the joint cartilage and underlaying subchondral bone (Martel-Pelletier, Tardif et al. 2000, Pelletier, Martel-Pelletier et al. 2000). In the progression of OA, the major proteinases involved in cartilage ECM destruction are MMP-13 for collagen and ADAMTS-4 and -5 for aggrecan (Flannery, Little et al. 1999, Singh, Marcu et al. 2019). Though, the synovium also contributes to the breakdown of cartilage (Dougados 1999, Dougados 2001). Joint inflammation and its mediators are demonstrated to play a role in symptoms and the progression as well (Pelletier, Martel-Pelletier et al. 2001). IL-1β and TNF-α are two major pro-inflammatory cytokines involved in the pathogenesis of OA (Huang, Ding et al. 2018). Secondary inflammation, irritation in periarticular tendon and ligament processes, stretching of the joint capsule, effusion upon irritation, pressure increases in the subchondral bone, and microfractures have all been attributed as causes for the eruption of OA pain (Steinmeyer and Konttinen 2006). Synovial fibroblasts may also play a role in the pathogenesis of RA and are involved in joint destruction (Hou, Li et al. 2001). However, the aberrant frequency of apoptotic cells can compromise normal tissue architecture and, in doing so, contribute to the loss of cell vitality. This is especially the case in explaining the loss of chondrocyte viability in arthritic conditions of synovial joints, such as RA and OA (Malemud 2018).

MMPs and ADAMTS disintegrin and metalloproteinase with thrombospondin motifs) are zinc-dependent proteolytic endopeptidases that play a crucial role in the destruction of extracellular matrix proteins and, the shedding of membrane-bound receptor molecules in various forms of arthritis and other diseases. MMP and ADAMTS production is increased under the influence of pro-inflammatory cytokines. They play a role in the maintenance of normal organ and tissue homeostasis (Malemud 2019).

MMP-13 or collagenase-3 is an interstitial collagen-degrading enzyme that has a relevance to the degradation of articular cartilage in RA and OA because it aggressively breakdown Type II collagen. High levels of MMP-13 have been found in arthritic tissues. ADAMTS-5 is the principle "aggrecanase" found in animal and human OA articular cartilage. The degradation of Type II collagen and aggrecan may constitute molecular and cellular events in the progression of RA and OA to joint failure (Malemud 2019). Thus, in the in vitro cartilage explant systems, the initial enzymes responsible for degrading aggrecan are aggrecanases, followed by MMPs at a later stage (Nagase and Kashiwagi 2003).

Pain is the most prominent symptom of OA. In OA, pain may be caused by mechanical and chemical stimuli. Articular cartilage does not have pain receptors and therefore it is not able to sense pain. Possible sources of pain in patients with OA include the synovial membrane, joint capsule, periarticular ligaments, periarticular muscle spasm, periosteum, and subchondral bone (Creamer and Hochberg 1997). Bone-related causes of pain include periostitis associated with osteophyte formation, subchondral microfractures, bone angina due to decreased blood flow and elevated intraosseous pressure, and bone marrow. Synovial causes of pain include irritation of sensory nerve endings within the synovium from osteophytes and synovial inflammation that is due, at least in part, to the release of prostaglandins, leukotrienes, and cytokines.

In addition to wear and tear on the joints, OA is associated with low-grade systemic and joint inflammation created by proinflammatory and matrix degrading cytokines. Chronic inflammation drives the progression of RA and OA to synovial joint failure. The inflammatory state in both musculoskeletal diseases is associated with significantly elevated levels of pro-inflammatory cytokines in joint synovial fluid, which is best exemplified by increases in IL-17 (Malemud 2018). By inhibiting IL-17 activity chondrocyte apoptosis may be prevented (Schminke, Trautmann et al. 2016). DEL-1 can protect chondrocytes from apoptosis in response to activators of either the intrinsic or extrinsic pathways, and to anoikis. (Wang, Tran et al. 2016, Wang, Boyko et al. 2018).

SUMMARY

2-Hydroxy-isocaproic acid (HICA), or an ester or amide derivative, an enantiomer or a pharmaceutically acceptable salt thereof, for use in prophylaxis and/or treatment of a disease or condition involving degradation of cartilage and/ or disruption of cartilage homeostasis and/or integrity is disclosed.

Further, a pharmaceutical composition for use in prophylaxis and/or treatment of a disease or condition involving degradation of cartilage and/or disruption of cartilage homeostasis and/or integrity is disclosed. The pharmaceutical composition may comprise 2-hydroxy-isocaproic acid (HICA) or an ester or amide derivative, an enantiomer or a pharmaceutically acceptable salt thereof, and one or more pharmaceutically acceptable carriers.

Further, a use of 2-hydroxy-isocaproic acid (HICA) or an ester or amide derivative, an enantiomer or a physiologically acceptable salt thereof in improving joint metabolism and/or increasing wellbeing of the joint is disclosed.

Further, a method for prophylaxis and/or treatment of a disease or condition involving degradation of cartilage and/ or disruption of cartilage homeostasis and/or integrity is disclosed. The method may comprise administering to a patient a therapeutically effective amount of 2-hydroxy-isocaproic acid (HICA) or an ester or amide derivative, an enantiomer or a pharmaceutically acceptable salt thereof.

BRIEF DESCRIPTION OF THE DRAWINGS

The accompanying drawings, which are included to provide a further understanding of the embodiments described in this specification and constitute a part of this specification, illustrate embodiments and together with the description help to explain the principles of the invention. In the drawings.

DETAILED DESCRIPTION

Figure 1:
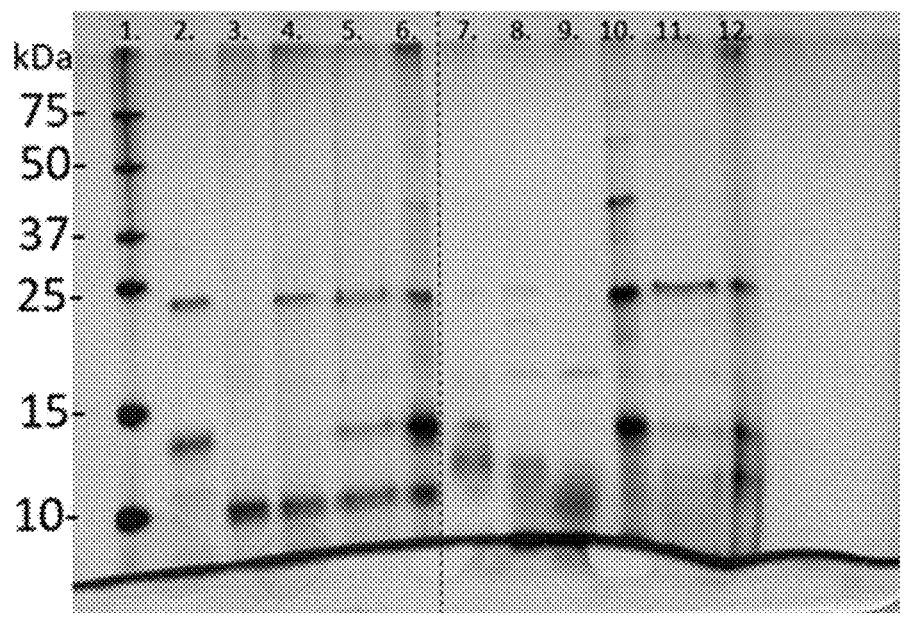
FIG. 1 illustrates the inhibition of recombinant human ADAMTS-5 and human Matrix metalloproteinase (MMP-13) mediated break-down of aggrecan by 10% rasemic D,L-α-hydroxy-isocaproic acid (HICA).

2-Hydroxy-isocaproic acid (HICA), or an ester or amide derivative, an enantiomer or a pharmaceutically acceptable salt thereof, for use in prophylaxis and/or treatment of a disease or condition involving degradation of cartilage and/ or disruption of cartilage homeostasis and/or integrity is disclosed.

2-Hydroxy-isocaproic acid (HICA) is also known as leucic acid, 2-hydroxy-4-methylvaleric acid, α-hydroxyisocaproic acid or 2-hydroxy-4-methylpentanoic acid, with a molecular weight of 132.16 g/mol and CAS Number 498-36-2. HICA is the 2-hydroxy-analogue of the essential amino acid leucine and is a physiological substance. It is a by-product of the leucine-acetyl-CoA pathway, specifically an end product of leucine metabolism in mammal incl. human tissues such as muscle and connective tissue. HICA is non-toxic.

Unless otherwise stated or depicted, 2-hydroxy-isocaproic acid are also meant to include all stereoisomeric (e.g. enantiomeric) forms of the structure; for example, the D and L configurations for each asymmetric center. Therefore, single stereochemical isomers as well as racemic, enantiomeric mixtures of 2-hydroxyisocaproic acid are within the scope of the present disclosure. Unless otherwise stated, all tautomeric forms or isotopic variants of 2-hydroxy-isocaproic acid are within the scope of the present disclosure.

HICA may be in a form of an ester or amide derivative. An ester or amide derivative of HICA may be pharmaceutically acceptable and possesses the desired pharmacological activity of HICA. Such ester or amide derivatives are non-toxic. The ester or amide derivative may be formed by a reaction of HICA with an alcohol or an amine. An ester or amide derivative of HICA may be physiologically acceptable; it may further possess the desired pharmacological activity of HICA.

A person skilled in the art is capable of selecting a suitable ester or amide derivative to achieve a required efficacy of HICA.

Ester derivatives of HICA may be formed or synthesized on the two reactive hydroxyl groups on the HICA molecule (i.e. on the 2-hydroxyl group and/or on the carboxyl group). Such ester derivatives may be pharmaceutically and/or physiologically acceptable and/or have the pharmacological activity of HICA. HICA prodrugs, which may be pharmaceutically acceptable ester derivatives of HICA (formed on the two reactive hydroxyl groups on the HICA molecule), may either spontaneously or enzymatically generate HICA. The ester derivative of HICA may be e.g. an alkyl ester (for example, a $C_1$-$C_6$ alkyl ester). The ester derivative of HICA may be formed by an esterification reaction between HICA and a $C_1$-$C_6$ alcohol (i.e. a reaction between the carboxylic group of HICA and the alcohol) or a $C_1$-$C_6$ carboxylic acid (i.e. a reaction between the 2-hydroxyl group of HICA and the carboxylic acid).

Amide derivatives of HICA may be formed or synthesized on the carboxylic acid HICA (i.e. on the carboxyl group of HICA) that are pharmaceutically acceptable and/or have the pharmacological activity of HICA. HICA prodrugs, which may be pharmaceutically acceptable amide derivatives of HICA (formed on the carboxylic acid HICA, i.e. on the carboxyl group of HICA) that either spontaneously or enzymatically generate (free) HICA.

The term "pharmaceutically acceptable salt" may refer to a salt of HICA that is pharmaceutically acceptable and that possesses the desired pharmacological activity of HICA. Such salts are non-toxic and may be inorganic or organic acid addition salts and/or base addition salts. Examples of ester derivatives of HICA include, but are not limited to: sodium, potassium, calcium, magnesium, ammonium, tetraalkylammonium, and the like. Suitable salts may include physiologically acceptable inorganic salts, such as ammonium, sodium, potassium, calcium, magnesium and/or similar salts, and/or physiologically acceptable organic salts. However, the pharmaceutical composition may comprise, in addition to HICA or its pharmaceutically acceptable salt, any other acceptable carrier(s), excipient(s) and/or additive(s), which may be necessary for the formulation of the final HICA preparation. Suitable additives may include a buffer, a flavor, an aromic agent, a sweetener, and the like.

In an embodiment, the disease or condition involving degradation of cartilage and/or disruption of cartilage homeostasis and/or integrity is osteoarthritis or related degenerative and/or inflammatory condition affecting joints.

In an embodiment, the disease or condition is the disease or condition is selected from the group consisting of osteoarthritis, rheumatoid arthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis. In an embodiment, the disease or condition is osteoarthritis. In an embodiment, the disease or condition is osteoarthritis or osteoarthritis including posttraumatic arthritis or a traumatic articular cartilage damage caused by any injury thereof.

In an embodiment, HICA is for use for reducing symptoms of affected joint incl. pain, stiffness and aches of a joint. The joint may be any joint in a subject.

In an embodiment, the disease or condition involving degradation of cartilage and/or disruption of cartilage homeostasis and/or integrity is mediated by ADAMTS-5 and/or MMP-13 and/or DEL-1.

In an embodiment, the disease or condition involving degradation of cartilage and/or disruption of cartilage homeostasis and/or integrity is prevented and/or treated by an inhibiting ADAMTS-5.

In an embodiment, osteoarthritis or related degenerative and/or inflammatory condition affecting joints is prevented and/or treated by the inhibition of ADAMTS-5.

Aggrecan is a large proteoglycan present in cartilage (in particular, articular cartilage), tendons, aorta wall, vertebrate discs, and the perineuronal net. In cartilage, aggrecan forms aggregates with link protein and hyaluronan. The ADAMTS family of secreted zinc metalloproteinases includes nineteen members that are known to bind and degrade extracellular cartilage matrix (ECM) components (Shiomi, Lemaitre et al. 2010). Several members of the ADAMTS family have been found to cleave aggrecan, the major proteoglycan component of cartilage.

ADAMTS-5 ablation may protect against cartilage damage and aggrecan loss after osteoarthritis induction through surgical instability of the medial meniscus (DMM) (Glasson, Askew et al. 2005). An antibody targeting ADAMTS-5 (Chiusaroli, Visintin et al. 2017) have been developed allowing the measurement of aggrecanase-derived cartilage neo-epitope levels in the synovial fluid as well as blood from rodents to human. This method revealed increased levels of ADAMTS-5 derived neo-epitope levels in the joints of rats in which cartilage degradation was induced by meniscal tear as well as in joints of OA patients (Chockalingam, Sun et al. 2011, Larsson, Lohmander et al. 2014).

The inhibition of ADAMTS-5 may prevent and/or treat cartilage damage and aggrecan loss. ADAMTS-5 is a protease responsible for aggrecan degradation, and blocking their activity inhibits both aggrecan and collagen degradation in response to IL-1. Blocking the activity of ADAMTS-5 may also have an analgesic effect (Malfait and Tortorella 2019). Blocking the activity of ADAMTS-5 may also maintain normal organ and tissue homeostasis. HICA may slow the progressive cartilage erosion by preventing aggrecan proteolysis by inhibiting aggrecanase activity. HICA may also inhibit structural damage, prevent or reduce long term disability and/or give symptomatic relief. HICA, as an ADAMTS-5 inhibitor, is capable of reaching the joint cartilage and may exert a protective effect on cartilage in diseases or conditions involving degradation of cartilage and/or disruption of cartilage homeostasis and/or integrity such as OA.

In an embodiment, the disease or condition involving degradation of cartilage and/or disruption of cartilage homeostasis and/or integrity is prevented and/or treated by an inhibition of MMP-13. In an embodiment, osteoarthritis or related degenerative and/or inflammatory condition affecting joints is prevented and/or treated by inhibition of MMP-13."

The pathologic feature seen in OA is gross articular cartilage damage (Wang, Sampson et al. 2013). Matrix metalloproteinases (MMP) are a family of calcium-dependent and zinc-containing endoproteinases, which share similar structural domains, but differ in substrate specificity, cell localizations, activation and inducibility. MMPs belong to the protease superfamily of metzincins. They have wider substrate specificity that in addition to ECM and basement membranes (BM) compound includes bioactive, non-matrix proteins of which the vast majority are bioactive molecules with targeted functions. MMPs are zinc-dependent endopeptidases that efficiently degrade the components of the ECM and BM. MMPs also process and release cytokines, chemokines, and growth factors from their proforms or their cryptic sites (Vilen, Salo et al. 2013). Patients with articular cartilage destruction have high MMP-13 expression (Roach, Yamada et al. 2005).

Collagenases are pleiotropic zinc endopeptidases/metalloproteinases and they can cleave the core matrisome proteins and non-matrix bioactive substrates including cytokines, chemokines, adhesion molecules, growth factors, and their receptors (Yoshihara, Nakamura et al. 2000, Mohan, Talmi-Frank et al. 2016). Many proteinases belonging to all classes of proteinases are expressed in joint tissues of patients with RA and OA. Among them, MMPs may have a role in the joint destruction in arthritis.

Cells of the cartilage, known as chondrocytes, maintain cartilage tissue homeostasis. They control the structural ECM assembly and regulate destructive, remodelling and reparative processes. In OA, cartilage-resident chondrocytes produce proteinases such as matrix metalloproteinases (e.g., MMP-13 and MMP-9), a metabolic imbalance may result in a failure of cartilage homeostasis and pathological cartilage destruction as well as eventual loss of cartilage (Barreto, Soininen et al. 2015).

The inhibition of MMP-13 may also prevent and/or treat cartilage damage and aggregan loss.

The inhibition of MMP-13 may prevent and/or treat cartilage damage and collagen loss. The inhibition of MMP-13 may prevent MMP-mediated degradation. MMP-13 is a proteolytic/collagenolytic enzyme that targets mature cartilage for degradation. Compared to other MMPs, the expression of MMP-13 is more restricted to connective tissue (Vincenti and Brinckerhoff 2002). It targets type II collagen in cartilage for degradation, and also degrades proteoglycans, types IV and type IX collagens, osteonectin and perlecan in cartilage (Shiomi, Lemaitre et al. 2010). Blocking the activity of MMP-13 may also maintain normal organ and tissue homeostasis and/or integrity.

The inhibition of MMP-13 decelerates articular cartilage loss. This prevents progression of osteoarthritis or related degenerative and/or inflammatory conditions affecting joints.

In an embodiment, the disease or condition involving degradation of cartilage and/or disruption of cartilage homeostasis and/or integrity is prevented and/or treated by preventing fragmentation of DEL-1.

Developmental endothelial locus-1 (DEL-1) is a 52-kDa glycoprotein that is secreted by endothelial cells and can associate with the endothelial cell surface and the extracellular matrix. DEL-1 is an endogenous inhibitor of leukocyte-endothelial adhesion limiting inflammatory neutrophil cell recruitment. It is a negative regulator of neutrophil extravasation that antagonizes β2-integrin-dependent adhesion onto the vascular endothelium (Choi, Chavakis et al. 2008).

DEL-1, an ECM-associated, integrin-binding protein, has a potent biological function in chondrocytes where it serves as an anti-apoptotic factor (Wang, Tran et al. 2016). Deletion of DEL-1 leads to decreased amounts of cartilage as measured by histomorphometry. DEL-1 knockout mice also have increased susceptibility to OA associated with increased chondrocyte apoptosis. Deletion of DEL-1 has been shown to increase severity of OA (Wang, Tran et al. 2016).

DEL-1 may act in an anti-inflammatory fashion (Choi, Chavakis et al. 2008). The periodontal tissue production of IL-17A is inhibited by DEL-1, whereas the expression of DEL-1 in endothelial cells is in turn inhibited by IL-17A. DEL-1 may act as a gatekeeper of leukocyte recruitment and inflammation. Another mechanism by which DEL-1 may suppress inflammation is through its ability to promote the clearance of platelet-derived microvesicles by the endothelium. DEL-1 may suppress the amplification of inflammatory cell recruitment mediated through chemokine release by infiltrating neutrophils. DEL-1 inhibits local inflammation in tissues that express it, by competing with the intra cellular adhesion molecule 1 (ICAM-1)-dependent firm adhesion and transmigration of neutrophils, as well as with their capacity for ICAM-1-dependent chemokine release that could amplify the recruitment of inflammatory cells. (Shin, Hosur et al. 2013)

DEL-1 may serve a mechanism by which a tissue self-regulates the local inflammatory response to prevent immunopathology (Eskan, Jotwani et al. 2012). DEL-1 may be required for homeostatic inhibition of inflammatory periodontal bone loss, which involves lymphocyte function-associated antigen 1 (LFA-1)-dependent neutrophil recruitment and IL-17R signalling. DEL-1 is an exemplar local regulatory factor in the context of tissue immune plasticity and inflammatory disorders (Hajishengallis and Chavakis 2019).

DEL-1 may inhibit IL-17-mediated inflammatory bone loss. It may also suppress LFA-1-dependent neutrophil recruitment and IL-17-triggered inflammatory pathology (Eskan, Jotwani et al. 2012). IL-17 is a cytokine capable of inducing the release of other cytokines, which can, in turn, contribute to tissue damage. Detectable levels of IL-17 have been reported in the synovial fluid from patients with rheumatic diseases (Kotake, Udagawa et al. 1999). IL-17 may be a proinflammatory cytokine capable of inducing release of chemokines by human chondrocytes and synovial fibroblasts. IL-17 may provide an additional step in unravelling mechanisms involved in the autocrine and paracrine pathways characterizing the activation of cartilage matrix degradation in OA (Honorati, Bovara et al. 2002).

In an embodiment, osteoarthritis or related degenerative and/or inflammatory condition affecting joints is prevented and/or treated by preventing fragmentation of DEL-1. DEL-1 inhibits IL-17-mediated inflammatory bone loss. It also suppresses LFA-1-dependent neutrophil recruitment and IL-17-triggered inflammatory pathology. DEL-1 may regulate both upstream (inflammatory cell recruitment) and downstream (osteoclastogenesis) events that lead to inflammatory bone loss. IL-17 is a cytokine capable of inducing the release of other cytokines, which can contribute to tissue damage.

By preventing fragmentation of DEL-1, HICA may prevent progression of inflammation such as acute and/or chronic inflammation and/or low-grade systemic inflammation and/or joint inflammation in osteoarthritis or related degenerative and/or inflammatory conditions affecting joints.

By preventing fragmentation of DEL-1, HICA may prevent cartilage degeneration in osteoarthritis or related degenerative and/or inflammatory condition affecting joints.

In an embodiment, the disease or condition involving degradation of cartilage and/or disruption of cartilage homeostasis and/or integrity is prevented and/or treated by the inhibition of MMP-13 and/or ADAMTS-5 and/or by prevention fragmentation of DEL-1.

HICA may be considered as a relative enzyme inhibitor. It may mediate its effect through multiple pathways damping down joint inflammation. HICA may also slow down joint cartilage degradation and also subsequent subchondral bone loss. HICA may also be considered as a symptom modulator, e.g. pain killer, since joint inflammation is one of the causes of the symptoms in degenerative and inflammatory joint conditions. HICA is a physiological substance in mammalian organisms including humans.

In an embodiment, symptoms of osteoarthritis or related degenerative and/or inflammatory condition affecting joints are prevented or treated. Examples of the symptoms include, but are not limited to, pain, reduced function, swelling, stiffness, joint enlargement, deformity, grinding, clicking, joint instability or buckling, muscle atrophy, weakness, joint effusion, crepitus, bony tenderness and enlargement, altered gait, limitation of motion, deformity, instability and the like.

In an embodiment, the pain is local and/or systemic pain. In an embodiment, the pain is joint pain, such as acute joint pain, chronic joint pain, inflammatory join pain and/or mechanical joint pain.

HICA may reduce pain, stiffness and aches of any joint and/or increase the mobility of a subject.

The terms "treat," "treating" or "treatment," and other grammatical equivalents as used herein, may include alleviating, inhibiting or reducing symptoms, reducing or inhibiting severity of, reducing incidence of, prophylactic treatment of, reducing or inhibiting recurrence of, preventing, delaying onset of, delaying recurrence of, abating or ameliorating or ameliorating a disease or condition symptoms, ameliorating the causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms may further include achieving a therapeutic benefit. By therapeutic benefit is meant eradication or amelioration of the underlying disease or condition being treated, and/or the eradication or amelioration of one or more of the physiological symptoms associated with the underlying disorder such that an improvement is observed in the subject.

The terms "prevent," "preventing" or "prevention," and other grammatical equivalents as used herein, may include preventing additional symptoms, preventing the causes of symptoms, inhibiting the disease or condition, e.g., arresting the development of the disease or condition and are intended to include prophylaxis. The terms may further include achieving a prophylactic benefit. For prophylactic benefit, the compositions are optionally administered to a subject at risk of developing a particular disease or symptom, to a subject reporting one or more of the physiological or pathological symptoms of a disease, or to a subject at risk of reoccurrence of the disease, to halter a progression of traumatic articular cartilage damage.

As used herein, the term "subject" may mean all or any mammals, including humans. Examples of subject include humans, cows, dogs, cats, goats, sheep, pigs, and rabbits.

The present disclosure relates also to a pharmaceutical composition comprising 2-hydroxy-isocaproic acid (HICA), or an ester or amide derivative, an enantiomer or a pharmaceutically acceptable salt thereof, and one or more pharmaceutically acceptable carrier for use in prevention and/or treatment of a disease or condition involving degradation of cartilage and/or disruption of cartilage homeostasis and/or integrity.

In an embodiment, the disease or condition involving degradation of cartilage and/or disruption of cartilage homeostasis and/or integrity is osteoarthritis or related degenerative and/or inflammatory condition affecting joints. In certain embodiments, the disease or condition is selected from the group consisting of osteoarthritis, rheumatoid arthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis. In an embodiment, disease or condition involving degradation of cartilage and/or disruption of cartilage homeostasis and/or integrity is mediated by ADAMTS-5 and/or MMP-13 and/or DEL-1. In an embodiment, the disease or condition involving degradation of cartilage and/or disruption of cartilage homeostasis and/or integrity is prevented and/or treated by the inhibition of MMP-13 and/or ADAMTS-5 and/or by prevention the fragmentation of DEL-1. In an embodiment, symptoms of osteoarthritis or related degenerative and/or inflammatory condition affecting joints are prevented or treated. In an embodiment, the pharmaceutical composition is for reducing pain, stiffness and aches of any joint and/or increasing the mobility of the subject.

In an embodiment, the pharmaceutical composition comprises 2-hydroxy-isocaproic acid (HICA) or an ester or amide derivative, an enantiomer or a pharmaceutically acceptable salt thereof, together with one or more pharmaceutically acceptable carriers and one or more additional therapeutic agents.

These therapeutic agents may include, but are not limited to immunoregulatory agents, non-steroidal anti-inflammatory drugs, steroids, human monoclonal antibodies, antipyretic drugs, hyaluronic acid, chondroitin sulphate or glucosamine in any form.

The pharmaceutical compositions may be manufactured in any manner known in the art, e.g., by means of conventional mixing, dissolving, granulating, dragee-making, levigating, emulsifying, encapsulating, entrapping or compression processes. "Pharmaceutically acceptable carrier" may refer to an excipient, carrier or additive that can be administered to a subject, together with HICA, and which does not destroy the pharmacological activity thereof and is generally safe, nontoxic and neither biologically nor otherwise undesirable when administered in doses sufficient to deliver a therapeutic amount of HICA. Suitable additives may include buffers, flavors, aromic agents, sweeteners and like.

In an embodiment, a therapeutically effective amount of 2-hydroxy-isocaproic acid (HICA), or an ester or amide derivative, an enantiomer or a pharmaceutically acceptable salt thereof is administered to the subject in need of prevention and/or treatment of a disease or condition involving degradation of cartilage and/or disruption of cartilage homeostasis and/or integrity.

The present disclosure relates also to a use of 2-hydroxy-isocaproic acid (HICA), or an ester or amide derivative, an enantiomer or a physiologically acceptable salt thereof, for improving joint metabolism and/or increasing wellbeing of the joint. The use for improving joint metabolism and/or increasing wellbeing of the joint may be regarded as a non-curative, nontherapeutic use or nutritional supplement.

In an embodiment, a physiologically effective amount of 2-hydroxy-isocaproic acid (HICA), or an ester or amide derivative, an enantiomer or a pharmaceutically acceptable salt thereof is administered to the subject in need of improving joint metabolism and/or increasing wellbeing of the joint.

2-Hydroxy-isocaproic acid (HICA) or an ester or amide derivative, an enantiomer or a pharmaceutically/physiologically acceptable salt thereof may be administered by any suitable route. These routes include, but are not limited to oral routes, intraduodenal routes, transdermal routes, subcutaneous routes, intranasal routes, parenteral injection (including intravenous, subcutaneous, intraperitoneal, intramuscular, intra-articular, intravascular or infusion), topical and rectal administration. A suitable dosage form for oral administration may be a solid dosage form, such as a tablet, depot tablet, capsule, granule, microgranule or powder, or a liquid dosage form, such as a solution or suspension. In certain embodiments, HICA or compositions described herein are administered orally. One solid dosage form for oral administration is a compressed or coated tablet. Other solid forms for oral administration are granules and powders, which can upon use be dissolved in a suitable liquid such as water, juice, milk, and like. Alternatively, HICA or compositions described herein can be in a form of drink mixes, bars, and soft gels and like. In certain embodiments, HICA or compositions described herein are administered transdermally. Forms for transdermal administration are salves, lotions or as patches and like. For the intraarticular, intramuscular or intravenous administration HICA may be dissolved in a solvent suitable for injection, such as physiological saline and/or alcohol. HICA may also be administered in sustained release forms or from sustained release drug delivery systems.

In one embodiment, HICA is to be administered to a subject orally. In one embodiment, HICA is to be administered to a subject transdermally. In one embodiment, HICA is to be administered to a subject by injection.

The terms "administer," "administering", "administration," and the like, as used herein, refer to the methods that may be used to enable delivery of HICA or compositions to the desired site of biological action.

In an embodiment, 2-hydroxy-isocaproic acid or an ester or amide derivative, a stereoisomer, an enantiomer or a pharmaceutically/physiologically acceptable salt thereof is to be administered to a subject in an amount of 5-100 mg/kg/day. However, the dosage may be higher or lower than these, since naturally the suitable dose may depend on the individual subject, the personal diet, age, gender, and other factors like diseases affecting gastrointestinal track. In an embodiment, HICA is to be administered to a subject in an amount which is sufficient to reach joint and particularly articular cartilage. In an embodiment, HICA is to be administered to a subject in an amount which is sufficient to reach synovium.

In one embodiment, HICA is to be administered to a subject in an amount of 10-40 mg/kg/day.

In one embodiment, HICA is to be administered to a subject in an amount of 15-20 mg/kg/day.

In one embodiment, HICA is to be administered to a subject in an amount of about 20 mg/kg/day.

The present disclosure relates also to a method for prevention and/or treatment of a disease or condition involving degradation of cartilage and/or disruption of cartilage homeostasis and/or integrity, wherein the method comprises administering to a subject a therapeutically effective amount of 2-hydroxy-isocaproic acid (HICA) or an ester or amide derivative, an enantiomer or a pharmaceutically/physiologically acceptable salt thereof.

In an embodiment, the disease or condition involving degradation of cartilage and/or disruption of cartilage homeostasis and/or integrity is osteoarthritis or related degenerative and/or inflammatory condition affecting joints. In certain embodiments, the disease or condition is the disease or condition is selected from the group consisting of osteoarthritis, rheumatoid arthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis. In an embodiment, disease or condition involving degradation of cartilage and/or disruption of cartilage homeostasis and/or integrity is modulated by ADAMTS-5 and/or MMP-13 and/or DEL-1. In an embodiment, the disease or condition involving degradation of cartilage and/or disruption of cartilage homeostasis and/or integrity is prevented and/or treated by the inhibition of MMP-13 and/or ADAMTS-5 and/or by prevention fragmentation of DEL-1. In an embodiment, symptoms of osteoarthritis or related degenerative and/or inflammatory condition affecting joints are prevented or treated. In an embodiment, the method is for use for reducing pain, stiffness and aches of any joint and/or increasing mobility of the subject.

In an embodiment, 2-hydroxy-isocaproic acid (HICA) or an ester or amide derivative, an enantiomer or a pharmaceutically/physiologically acceptable salt thereof, is for use in the manufacture of a medicament for prevention and/or treatment of a disease or condition involving degradation of cartilage and/or disruption of cartilage homeostasis and/or integrity.

In an embodiment, provided is a method for prevention and/or treatment of a disease or condition involving degradation of cartilage and/or disruption of cartilage homeostasis and/or integrity in a subject in need thereof, comprising administering an effective amount of pharmaceutical composition provided herein to the subject.

EXAMPLES

Example 1

ADAMTS-5

This experiment was carried out to demonstrate inhibition of recombinant human ADAMTS-5 (Aggrecanase 2, #CC1034, Chemicon, International. Inc.) and human Matrix metalloproteinase 13 (MMP-13, #30100802, BioTeZ, Berlin-Buch, Berlin, Germany) mediated break down of aggrecan (CC1890, Sigma-Aldrich, Darmstadt, Germany) by 10% rasemic D,L-α-hydroxy-isocaproic acid (HICA, Leios OÜ, Tallinn, Estonia) at pH 7.4. As positive inhibitor controls Ilomastat (Ilo, CC1010, Millipore) and chlorhexidine (CHX, Corsodyl®, [2 mg/ml] (GlaxoSmithKline, Brøndby, Denmark) were used and 50 mM Tris-HCl-buffer (TNC): pH 7.5; 0.2 M NaCl; 1.0 mM CaCl$_2$) was used as neutral assay buffer.

MMP-13 was preincubated 1 hour at 37° C. with p-aminophenylmercuric acetate (APMA, A9563, Sigma-Aldrich) to optimally activate (pro)MMP-13. As substrate, Aggrecan was added and then ADAMTS-5 or activated MMP-13 as catalytic/proteolytic enzyme and TNC, as neutral control, and 10% HICA, CHX or Ilo as protease/MMP-inhibitors let incubated together from 1 hour (h) to 2 days (d). The enzyme reactions terminated by boiling with modified Laemmli buffer. The samples were analysed by 8% SDS-PAGE and after electrophoresis the defragmentation of Aggrecan was visualised using Silver Stain Pierce®.

Sample with concentrations in lines:
1. 0.25 μl molecular weight standards. Bio-Rad
2. 4.2 μl Aggrecan (0.5 μg/μl)
3. 4 μl ADAMTS-5 (0.1 μg/μl)
4. 4.2 μl Aggrecan+4 μl ADAMTS-5+6 μl TNC-buffer. inc: 2d
5. 4.2 μl Aggrecan+4 μl ADAMTS-5+6 μl 10% HICA. inc: 2d
6. 4.2 μl Aggrecan+4 μl ADAMTS-5+6 μl CHX (2 mg/ml). inc: 2d
7. 1 μl MMP-13 (0.2 μg/μl)+3 μl 2 mM APMA+6 μl TNC
8. 4.2 μl Aggrecan+1 μl MMP-13 (0.2 μg/μl)+3 μl 2 mM APMA+6 μl TNC. inc: 1h
9. 4.2 μl Aggrecan+1 μl MMP-13 (0.2 μg/μl)+3 μl 2 mM APMA+6 μl TNC. inc: 2d
10. 4.2 μl Aggrecan+1 μl MMP-13 (0.2 μg/μl)+3 μl 2 mM APMA+6 μl CXH. inc: 2d
11. 4.2 μl Aggrecan+1 μl MMP-13 (0.2 μg/μl)+3 μl 2 mM APMA+6 μl 10% HICA. inc: 2d
12. 4.2 μl Aggrecan+1 μl MMP-13 (0.2 μg/μl)+3 μl 2 mM APMA+6 μl Ilo. inc: 2d FIG. 1 shows that 10% HICA inhibited the break down of Aggrecan by both ADAMTS-5 and MMP-13 proteases (line 5 and 11, respectively). FIG. 1 shows that HICA prevents break down of aggrecan. Therefore, both ADAMTS-5 and MMP-13 may be considered to modulate enzyme activity rather than prevent enzyme activity like chlorhexidine in our study.

Example 2

This example was carried out to test the inhibition of the catalytic activity of MMP-13. MMP-13 activity was measured as described previously (Hanemaaijer, Visser et al. 1998). In brief, MMP-13 was captured from biological fluids using MMP-13-specific monoclonal antibody-coated 96-well plates. The wells were washed three times with PBS-T (phosphate buffered saline solution containing 0.05% [v/v] Tween-20) and incubated with 125-pl assay buffer (50 mM Tris-HCl, pH 7.6. 150 mM NaCl, 5 mM CaCl$_2$, 1 μM ZnCl$_2$ and 0.01% [v/v] Brij-35), to which 15 μl (50 μg/ml) modified pro-urokinase (UKcol) and 10 pl (6 mM stock) chromogenic substrate S-2444 was added. Color development was recorded by measurement of A405 using a Titertek Multiskan 8-channel photometer (Verheijen, Nieuwenbroek et al. 1997). For measurement of total activity (already active plus latent MMP-13) in biological fluid, the immobilized MMP-13 was incubated with assay buffer containing 0.5 mM APMA for 2 hr, after which UKcol and S-2444 were added and activity was recorded. (Hanemaaijer, Sier et al. 1999)

The protocol for this experiment: MMP-13 was activated with 0.5 nM of APMA (p-aminophenylmercuric acetate, obtained from Sigma-Aldrich #A9563), after which MMP-13 was diluted and mixed with indicated inhibitors. Solution was let to incubate 30 minutes at 37° C. Detection enzyme was added with substrate and measure A405 in time (incubate between measurements at 37° C. in a humified chamber). Calculate DeltaA/t^2*1000

Figure 2:
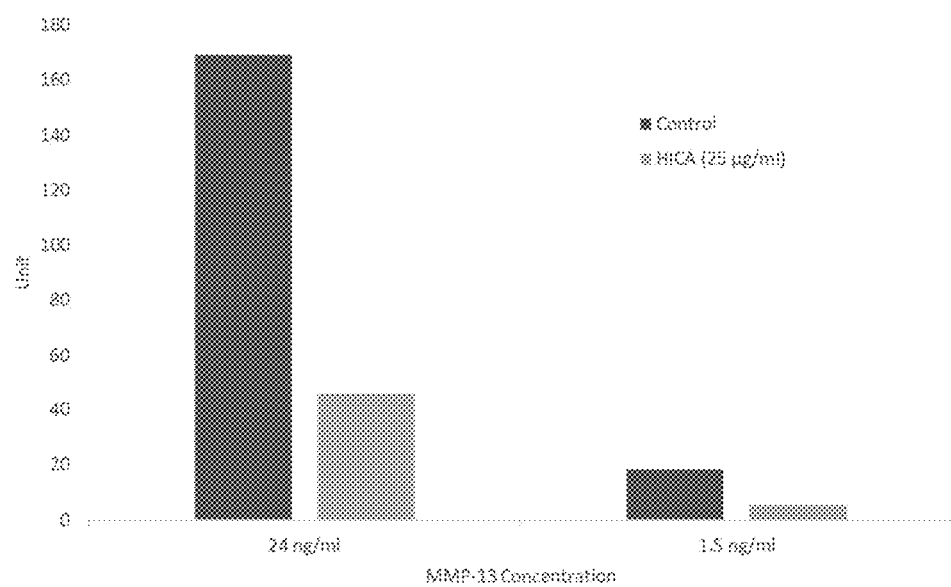
FIG. 2 illustrates the inhibition of Matrix metalloproteinase 13 (MMP-13) mediated break-down of collagen by HICA.

Inhibition of MMP-13 mediated break down of collagen by rasemic α-hydroxy-isocaproic acid (HICA) is shown in FIG. 2. HICA was found to exert effective inhibition of the activity of MMP-13 at a concentration level 25 μg/ml. At 24 ng/ml MMP-13 concentration there was 73% decreased activity noted and with 1.5 ng/ml concentration 72% decrease.

Example 3

This example was carried out to test the inhibition of the MMP-8 mediated DEL-1 fragmentation by D-HICA and L-HICA (Study A) and dose-dependently inhibition effect of D-HICA (Study B).

The degradation of DEL-1 by MMP-8 was determined similarly as described (DeCarlo 1994, Sorsa, Salo et al. 1997). Human recombinant pure MMP-8 (#30100702, Proteaimmun) was preincubated 1 hour at 37° C. with p-aminophenylmercuric acetate (APMA) and different HICA isomers (D-HICA, #CAS 20312-37-2, Santa Cruz Biotechnology; L-HICA, #219827 Sigma-Aldrich). After which DEL-1 was added as a substrate. That was let incubate overnight at +37° C. Analyzed on ii % SDS-PAGE with Silver Stain Pierce®. α-hydroxy-isovaleric acid (HMB). Ilomastat (Ilo). As assay buffer 50 mM Tris-HCl-buffer (TNC): pH 7.5; 0.2 M NaCl; 1.0 mM CaCl$_2$ (Tervahartiala, Ingman et al. 1995). Fragmentation of DEL-1 induced by MMP-8 treated with 1 mM APMA was regarded as 100%. (Sorsa, Salo et al. 1997).

Figure 3A:
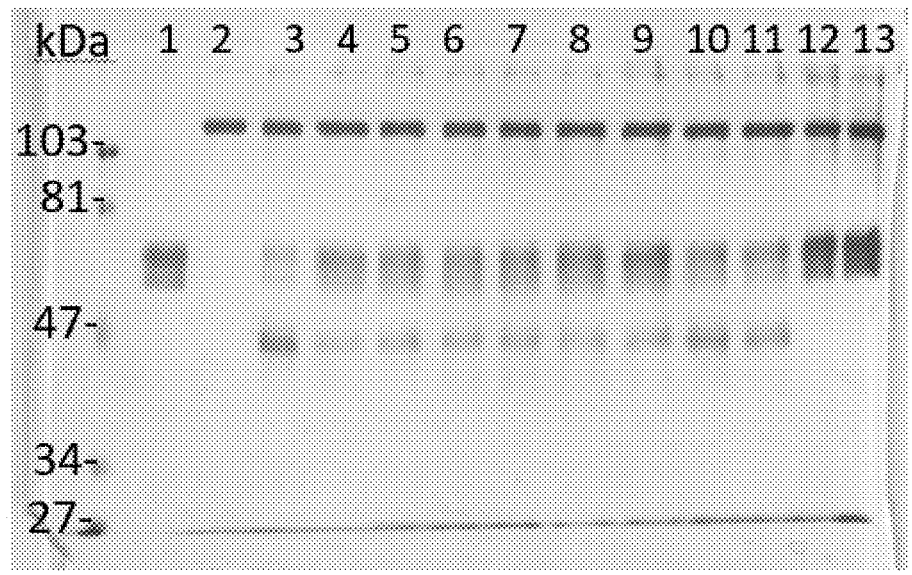
FIG. 3A illustrates the inhibition of the MMP-8 mediated DEL-1 fragmentation by L-HICA and D-HICA.
Figure 3B:
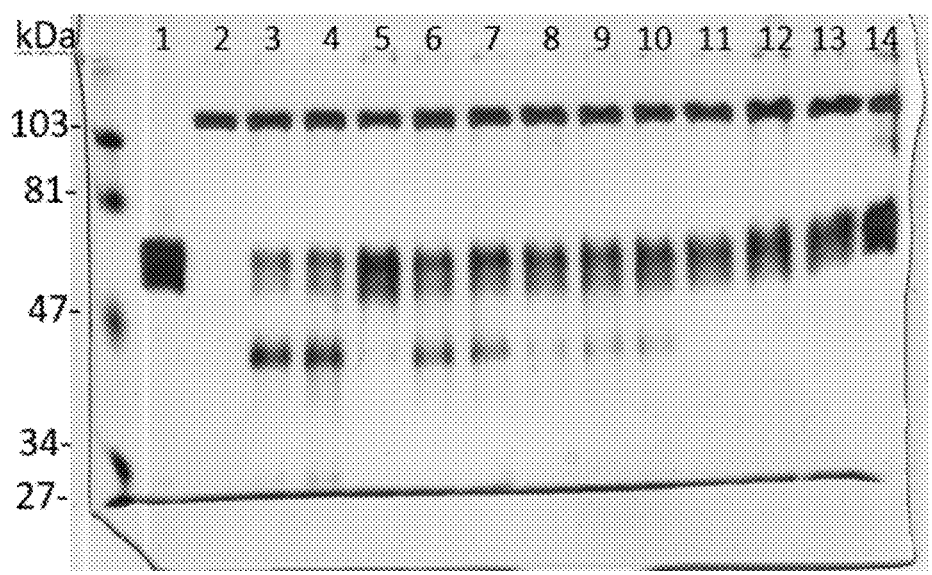
FIG. 3B illustrates the inhibition of the MMP-8 mediated DEL-1 fragmentation dose dependently by D-HICA.

Sample with concentrations in lines:
Study A:
1. 1.7 μl DEL-1 (0.2 μg/μl)
2. 1 μl MMP-8 (0.1 μg/μl)+5 μl 2 mM APMA+4 μl TNC
3. 1.7 μl DEL-1 (0.2 μg/μl)+1 μl MMP-8 (0.1 μg/μl)+5 μl 2 mM APMA+4 μl TNC
4.,5. 1.7 μl DEL-1 (0.2 μg/μl)+1 μl MMP-8 (0.1 μg/μl)+5 μl 2 mM APMA+10% 4 μl D-HICA
6.,7. 1.7 μl DEL-1 (0.2 μg/μl)+1 μl MMP-8 (0.1 μg/μl)+5 μl 2 mM APMA+10% 4 μl L-HICA
8.,9. 1.7 μl DEL-1 (0.2 μg/μl)+1 μl MMP-8 (0.1 μg/μl)+5 μl 2 mM APMA+10% 4 μl D-HMB
10.,11. 1.7 μl DEL-1 (0.2 μg/μl)+1 μl MMP-8 (0.1 μg/μl)+5 μl 2 mM APMA+10% 4 μl L-HMB
12.,13. 1.7 μl DEL-1 (0.2 μg/μl)+1 μl MMP-8 (0.1 μg/μl)+5 μl 2 mM APMA+4 μl Ilo
Study B:
1. 1.7 μl DEL-1 (0.2 μg/μl)
2. 1 μl MMP-8 (0.1 μg/μl)+5 μl 2 mM APMA+4 μl TNC
3.,4. 1.7 μl DEL-1 (0.2 μg/μl)+1 μl MMP-8 (0.1 μg/μl)+5 μl 2 mM APMA+4 μl TNC
6.,7. 1.7 μl DEL-1 (0.2 μg/μl)+1 μl MMP-8 (0.1 μg/μl)+7 μl 1.4 mM APMA+2 μl 10% D-HICA
8.,9.,10. 1.7 μl DEL-1 (0.2 μg/μl)+1 μl MMP-8 (0.1 μg/μl)+5 μl 2 mM APMA+4 μl 10% D-HICA 11., 12., 13. 1.7 µl DEL-1 (0.2 µg/µl)+1 µl MMP-8 (0.1 µg/µl)+1 µl 10 mM APMA+8 µl 10% D-HICA 14. 1.7 µl DEL-1 (0.2 µg/µl)+1 µl MMP-8 (0.1 µg/µl)+5 µl 2 mM APMA+4 µl Ilo FIG. 3A shows that both HICA isomers inhibit the proteolytic activity or DEL-1 degradation of MMP-8 (A). FIG. 3B shows that D-HICA inhibit MMP-8 dose-dependently. This shows that D-HICA and L-HICA were able to prevent fragmentation of DEL-1 by inhibiting MMP-8. Therefore, HICA, by MMP-8 inhibition, can maintain the effect of DEL-1 and/or promote DEL-1's effect on inflammation.

Example 4

In order to assess the effects of HICA on type II collagen and hyaluronic acid in healthy adults in vivo a study was conducted, where fifteen healthy male athletes (age 21.3±2.8 yr) volunteered for the 4-week study with double-blind design (Table 1). They were randomized to two parallel groups. Subjects in Group 1 (n=8, age 22.8±4.6 yr, height 179±6 cm, weight 76.2±6.9 kg, fat % 14.1±3.7%) received 583.2 mg of sodium salt of HICA (corresponding 500 mg of HICA) thrice a day for 4 weeks, and those in Group 2 (n=7, age 21.3±3.0 yr, height 178±5 cm, weight 73.5±5.0 kg, fat % 11.1±3.0%) received placebo (650 mg of maltodextrin) thrice a day for the same period. The subjects and the controls received repacked substance of equal volume (1.5 ml) which they were advised to mix with liquid. The subjects and the controls kept physical training constant during the study period, and they kept training daily. Serum specimens were obtained at baseline and in the end of the treatment. Specimens were aliquoted and immediately frozen; serum was collected and frozen at −70° C.

TABLE 1

The Characteristics of the subjects (Mean ± SD) before and after four weeks on HICA or placebo

|  | Before HICA | After HICA | Before placebo | After placebo | ANOVA between treatments |
| --- | --- | --- | --- | --- | --- |
| Height (cm) | 178 ± 6.4 |  | 178 ± 4.7 |  |  |
| Weight (kg) | 76.2 ± 6.9 | 76.5 ± 8.4 | 73.5 ± 5.0 | 73.7 ± 5.0 | p = n.s. |
| Body Fat procent (%) | 14.1 ± 3.7 | 14.0 ± 2.5 | 11.1 ± 3.0 | 11.3 ± 2.5 | p = n.s. |
| Hemoglobin (g/l) | 152 ± 7 | 151 ± 5 | 151 ± 7 | 146 ± 5 | p = n.s. |
| Hematocrite | 0.44 ± 0.02 | 0.45 ± 0.02 | 0.43 ± 0.03 | 0.42 ± 0.02 | p = n.s. |

HICA = DL-α-hydroxy-isocaproic acid

C2C and hyaluronic acid (HA) were used as serum markers in the study.

C2C

Cartilage biomarkers exist for the measurement of cartilage matrix turnover and may reveal differences in patients with degenerative joint condition. C2C is a biomarker of cartilage degradation and re-modelling, a process that is found in children and adults with OA and RA. The C2C assay measures the amount of real-time collagen degradation in serum. In all kind of degenerative joint conditions type II collagen is extensively cleaved and destroyed by the activities of collagenases, which results in loss of type II collagen. The collagenase-3 (MMP-13) is included in the cleavage of type II collagen triple helix and, hence, generate the collagen neoepitope C2C (Manicourt, Azria et al. 2006). The determination of C2C in serum of arthritic patients may be used for the detection of oxidative-related cartilage degradation episode. Further, these markers may be used for monitoring the effects of anti-inflammatory or antioxidant drugs on the cartilage degradation (Deberg, Labasse et al. 2005).

The C2C may be used as an indicator of early changes in cartilage metabolism which predicts the hidden onset of radiographic changes characteristic of OA, i.e. pre-arthritic changes in the cartilaginous collagen II (Chu, Lopez et al. 2002). The integrity of the collagen II network of cartilage may also be compromised soon after joint injury.

Mullan et al. (Mullan, Matthews et al. 2007) demonstrated that early changes in serum biomarkers of type I collagen and cartilage type II collagen turnover during biologic therapy are significantly associated with subsequent radiographic progression in a prospective cohort of patients with erosive inflammatory joint arthritis. The biomarker for degradation of collagen (C2C) rather than for the synthesis of cartilage collagen, was significantly elevated in patients with rapid radiographic progression when compared with patients with slow progression. The development of radiographic damage during the first years after diagnosis may be a reflection of increased degradation of collagen and enhanced turnover of proteoglycans rather than a lack of newly synthesized of cartilage collagen, i.e. production of reparative neo collagen II substratum (Verstappen, Poole et al. 2006).

HA is a glycosaminoglycan formed from alternating units of glucosamine and glucuronic acid. It is a high molecular weight (1000-5000 kD) anionic polysaccharide composed of repeating disaccharides of glucuronate acetylglucosamine. It is a constituent of synovium and cartilage and is thought to contribute to the lubricating mechanisms of synovial fluid. The components that make synovial lymph unusual are HA and lubricin, 2 biopolymers actively secreted by the synovial lining cells. The HA of synovial fluid from diseased joints, especially in RA, is depolymerized, and the fluid no longer exhibits a non-Newtonian flow behaviour, which may be detrimental to the lubrication mechanism (Garnero, Rousseau et al. 2000).

As a major product of synovial cells, HA is considered a marker of synovitis. HA can be measured by assaying the specific binding of the G1 domain of aggrecan to it.

Local increased production of HA has been demonstrated in inflamed synovium from patients with RA, OA, ankylosing spondylitis, and reactive arthritis (Wells, Klareskog et al. 1992). HA levels are increased in patients with RA, and the highest levels have been found in patients with aggressive disease of both large (hip) and small (hands and feet) joints (Krueger, Fields et al. 1990, Fex, Eberhardt et al. 1997). Baseline levels were higher in accelerated disease and cartilage destruction. Thus, the serum HA level may be a potent prognostic marker of joint destruction in RA and OA (Garnero, Rousseau et al. 2000). Serum HA levels may predict disease outcome in OA of the knee. Increased serum HA levels have been reported in patients with OA (Georges, Vigneron et al. 1997) and it may be used in predicting disease outcome in knee OA (Sharif, George et al. 1995) and hip OA (Mazieres, Garnero et al. 2006). These associations with OA in varying stages of disease suggest that HA may be useful as a biomarker in studies of therapeutic interventions for OA. Although lower than in RA, increased HA levels were also found in patients with knee OA. Baseline levels were higher in accelerated disease and cartilage destruction (Sharif, George et al. 1995). The serum HA level may be a potent prognostic marker of joint destruction in RA and OA (Garnero, Rousseau et al. 2000). It may also correlate with severity of the symptoms.

Plasma levels of HA do not significantly correlate with plasma levels of PMN/neutrophil elastase. HA is a marker in arthritis because it reflects synovial involvement and inflammation rather than inflammation only (Goldberg, Huff et al. 1991). HA levels correlate with objective functional capacity score and with an articular index based on the total amount of cartilage in the involved joints (Pelletier, Martel-Pelletier et al. 2001).

Serum Analyses

A kit for determination of the type II collagen C2C neoepitope was provided by Ibex Technologies (Montreal, Quebec, Canada). It was measured by means of an enzyme-linked immunosorbent assay (ELISA) (Kojima, Mwale et al. 2001). It uses a monoclonal antibody that recognizes a sequence near the carboxy terminus of the ¾ piece (Hunter, Li et al. 2007). The assay range was 10-500 ng/ml, the intra- and inter-assay coefficients of variation of the serum C2C assay were 6.7% and 6.7%, respectively, and the normal range was 5-20 ng/ml.

Serum HA was measured by Hyaluronan Enzyme-Linked Immunosorbent Assay Kit, HA-ELISA (Echelon Biosciences Inc., Salt Lake City, USA). Intra- and interassay coefficients of variation of the serum HA assay were 3.2% and 4.42% respectively. The assay range was 15-1,000 ng/ml, the intraassay CV was <4%, the interassay CV was <6%.

The Analysis of Variance (ANOVA) was used to assess statistical differences between the treatment groups. Data were handled as changes between the measurements before and after the treatments. Further, paired t-test was used to compare values before and after treatments. Probabilities less than 0.05 were regarded as statistically significant. Statistical analyses were carried out using the software program Systat for Windows (Statistics, Version 9, Evanston, IL, USA, 1992). The results are presented as means±SEM.

There were no differences between the characteristics of the groups (Table 1).

Table 2 shows the serum concentrations of markers of bone metabolism and articular cartilage (Mean±SEM) before and after four weeks on HICA or placebo.

Figure 4:
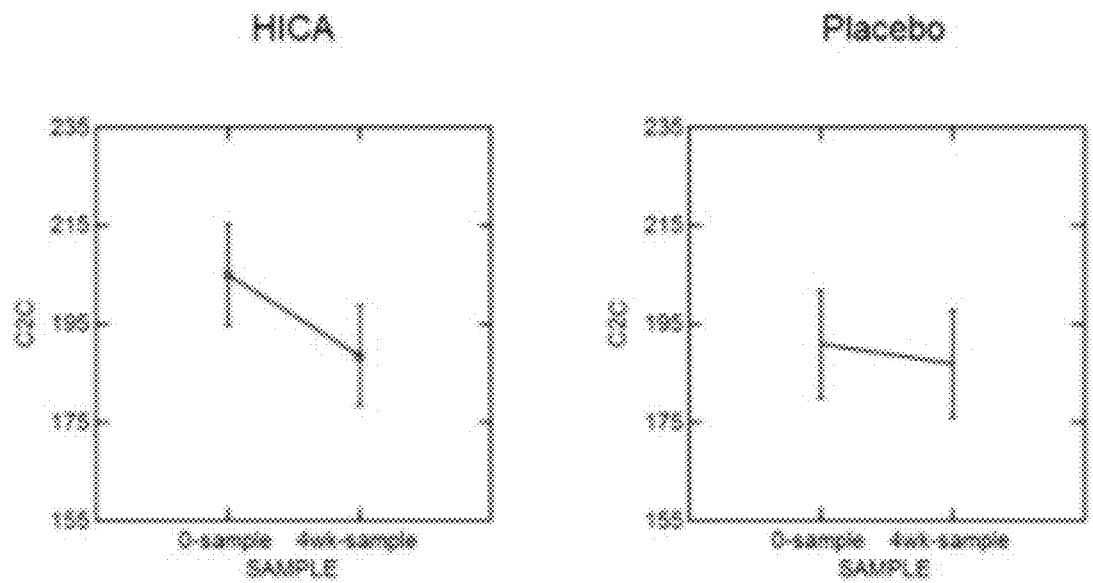
FIG. 4 illustrates the in vivo serum concentrations of markers of joint metabolism, C2C and HA, before and after four weeks on (HICA) or placebo administration.
Figure 4:
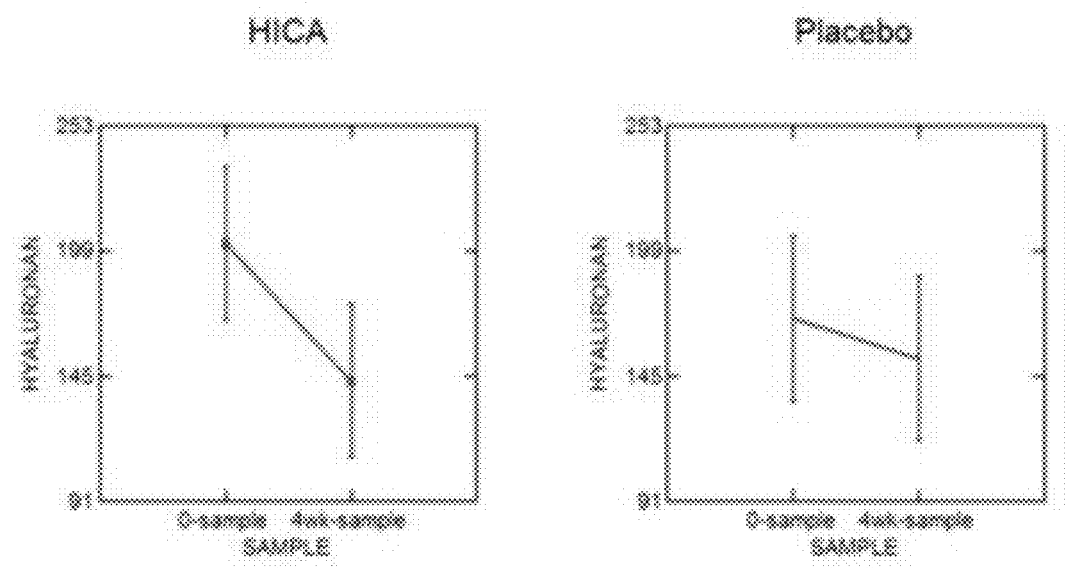

Table 2 and FIG. 4 show that there was 29% decrease in serum HA concentration during 4-week administration of HICA and 10% decrease after the same period on placebo ($p=0.066$ between the groups, ANOVA). Similarly, C2C decreased 8% in the HICA group and 2% in placebo group ($p=0.069$ between the groups, ANOVA). Serum HA and C2C decreased after HICA administration. The results when compared to placebo did not reach the conventional limit of $p<0.05$ of significance but indicate a marked tendency between the treatments.

The study group consisted healthy male athletes which did not have a history of arthritic conditions and they did not experience any symptoms of osteoarthritis or related condition. Therefore, it can be assumed that they did not have stimulated degenerative articular metabolism. Their joints' cartilages were not under degenerative process. Plasma levels of HA does not significantly correlate with plasma levels of human neutrophil elastase or with the erythrocyte sedimentation rate. Therefore, HICA mediates its effect through MMP inhibition and/or through anti-inflammatory effect which is potentiated by protecting the DEL-1 from fragmentation. HICA mediates also its effect through ADAMTS-5 inhibition and/or through anti-inflammatory effect which is potentiated by protecting the DEL-1 from fragmentation.

The main objectives in the management of OA and related degenerative joint diseases are to reduce symptoms, minimize functional disability, and limit progression and development of the structural changes. By this way already early pre-arthritic sneaking symptoms can be prevented by HICA administration. Hyaluronic acid is unique as a marker, in that it is a reflection of synovial involvement and inflammation, rather than only of inflammation, in any kind arthritis (Goldberg, Huff et al. 1991). HA has been reported to be elevated in OA, and HA levels were found to correlate with an objective functional capacity score and with an articular index based on the total amount of cartilage in the involved joints (Pelletier, Martel-Pelletier et al. 2001). Therefore, decreased HA and C2C concentrations may decrease the risk of degenerative joint disease and the symptoms including joint pain as well.

HA may restrict pain-triggering molecules which may enhance normal production of HA from synovial sites. Other mechanism may be involved in order to increase HA and tamper inflammation (Pelletier, Martel-Pelletier et al. 2001).

The embodiments described hereinbefore may be used in any combination with each other. Several of the embodiments may be combined together to form a further embodiment. A product for use or a method, to which the invention is related, may comprise at least one of the embodiments described hereinbefore. It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item refers to one or more of those items. The term "comprising" is used in this specification to mean including the feature(s) or act(s) followed thereafter, without excluding the presence of one or more additional features or acts.

It is obvious to a person skilled in the art that with the advancement of technology, the basic idea of the invention may be implemented in various ways. The invention and its

TABLE 2

| | Before HICA | After HICA | Before placebo | After placebo | ANOVA between treatments |
|---|---|---|---|---|---|
| S-Hyaluronan ng/ml | 202 ± 56 | 143 ± 19 | 169 ± 21 | 153 ± 19 | p = 0.066 |
| S-C2C ng/ml | 204 ± 14 | 189 ± 10 | 191 ± 4 | 187 ± 11 | p = 0.069 | embodiments are thus not limited to the examples described above; instead, they may vary within the scope of the claims.

REFERENCES

Anderson, D. D., S. Chubinskaya, F. Guilak, J. A. Martin, T. R. Oegema, S. A. Olson and J. A. Buckwalter (2011). "Post-traumatic osteoarthritis: improved understanding and opportunities for early intervention." J Orthop Res 29(6): 802-809.

Barreto, G., A. Soininen, P. Ylinen, J. Sandelin, Y. T. Konttinen, D. C. Nordstrom and K. K. Eklund (2015). "Soluble biglycan: a potential mediator of cartilage degradation in osteoarthritis." Arthritis Res Ther 17: 379

Berenbaum, F. (2013). "Osteoarthritis as an inflammatory disease (osteoarthritis is not osteoarthrosis!)." Osteoarthritis Cartilage 21(1): 16-21.

Chiusaroli, R., M. Visintin, G. Caselli and L. C. Rovati (2017). Anti-ADAMTS-5 antibody, derivatives and uses thereof, Google Patents.

Chockalingam, P., W. Sun, M. Rivera-Bermudez, W. Zeng, D. Dufield, S. Larsson, L. S. Lohmander, C. Flannery, S. Glasson and K. Georgiadis (2011). "Elevated aggrecanase activity in a rat model of joint injury is attenuated by an aggrecanase specific inhibitor." Osteoarthritis and cartilage 19(3): 315-323.

Choi, E. Y., E. Chavakis, M. A. Czabanka, H. F. Langer, L. Fraemohs, M. Economopoulou, R. K. Kundu, A. Orlandi, Y. Y. Zheng, D. A. Prieto, C. M. Ballantyne, S. L. Constant, W. C. Aird, T. Papayannopoulou, C. G. Gahmberg, M. C. Udey, P. Vajkoczy, T. Quertermous, S. Dimmeler, C. Weber and T. Chavakis (2008). "Del-1, an endogenous leukocyte-endothelial adhesion inhibitor, limits inflammatory cell recruitment." Science 322(5904): 1101-1104.

Chu, Q., M. Lopez, K. Hayashi, M. Ionescu, R. C. Billinghurst, K. A. Johnson, A. R. Poole and M. D. Markel (2002). "Elevation of a collagenase generated type II collagen neoepitope and proteoglycan epitopes in synovial fluid following induction of joint instability in the dog." Osteoarthritis Cartilage 10(8): 662-669.

Creamer, P. and M. C. Hochberg (1997). "Osteoarthritis." Lancet 350(9076): 503-508.

Deberg, M., A. Labasse, S. Christgau, P. Cloos, D. Bang Henriksen, J. P. Chapelle, B. Zegels, J. Y. Reginster and Y. Henrotin (2005). "New serum biochemical markers (Coll 2-1 and Coll 2-1 NO2) for studying oxidative-related type II collagen network degradation in patients with osteoarthritis and rheumatoid arthritis." Osteoarthritis Cartilage 13(3): 258-265.

Dougados, M. (1999). "Evaluation of disease progression during nonsteroidal antiinflammatory drug treatment: imaging by arthroscopy." Osteoarthritis Cartilage 7(3): 345-347.

Dougados, M. (2001). "The role of anti-inflammatory drugs in the treatment of osteoarthritis: a European viewpoint." Clin Exp Rheumatol 19(6 Suppl 25): S9-14.

Eskan, M. A., R. Jotwani, T. Abe, J. Chmelar, J. H. Lim, S. Liang, P. A. Ciero, J. L. Krauss, F. Li, M. Rauner, L. C. Hofbauer, E. Y. Choi, K. J. Chung, A. Hashim, M. A. Curtis, T. Chavakis and G. Hajishengallis (2012). "The leukocyte integrin antagonist Del-1 inhibits IL-17-mediated inflammatory bone loss." Nat Immunol 13(5): 465-473.

Felson, D. T. (2014). "Osteoarthritis: priorities for osteoarthritis research: much to be done." Nat Rev Rheumatol 10(8): 447-448.

Fex, E., K. Eberhardt and T. Saxne (1997). "Tissue-derived macromolecules and markers of inflammation in serum in early rheumatoid arthritis: relationship to development of joint destruction in hands and feet." Br J Rheumatol 36(11): 1161-1165.

Flannery, C. R., C. B. Little, C. E. Hughes and B. Caterson (1999). "Expression of ADAMTS homologues in articular cartilage." Biochemical and biophysical research communications 260(2): 318-322.

Fosang, A. J., K. Last, V. Knäuper, G. Murphy and P. J. Neame (1996). "Degradation of cartilage aggrecan by collagenase-3 (MMP-13)." FEBS letters 380(1-2): 17-20.

Garnero, P., J. C. Rousseau and P. D. Delmas (2000). "Molecular basis and clinical use of biochemical markers of bone, cartilage, and synovium in joint diseases." Arthritis Rheum 43(5): 953-968.

Georges, C., H. Vigneron, X. Ayral, V. Listrat, P. Ravaud, M. Dougados, M. Sharif, P. Dieppe and T. Saxne (1997). "Serum biologic markers as predictors of disease progression in osteoarthritis of the knee." Arthritis Rheum 40(3): 590-591.

Glasson, S. S., R. Askew, B. Sheppard, B. Carito, T. Blanchet, H.-L. Ma, C. R. Flannery, D. Peluso, K. Kanki and Z. Yang (2005). "Deletion of active ADAMTS5 prevents cartilage degradation in a murine model of osteoarthritis." Nature 434(7033): 644.

Goldberg, R. L., J. P. Huff, M. E. Lenz, P. Glickman, R. Katz and E. J. Thonar (1991). "Elevated plasma levels of hyaluronate in patients with osteoarthritis and rheumatoid arthritis." Arthritis Rheum 34(7): 799-807.

Guilak, F., R. J. Nims, A. Dicks, C.-L. Wu and I. Meulenbelt (2018). "Osteoarthritis as a disease of the cartilage pericellular matrix." Matrix Biology 71: 40-50.

Hajishengallis, G. and T. Chavakis (2019). "DEL-1-Regulated Immune Plasticity and Inflammatory Disorders." Trends in molecular medicine.

Hanemaaijer, R., H. Visser, Y. T. Konttinen, P. Koolwijk and J. H. Verheijen (1998). "A novel and simple immunocapture assay for determination of gelatinase-B (MMP-9) activities in biological fluids: saliva from patients with Sjogren's syndrome contain increased latent and active gelatinase-B levels." Matrix Biol 17(8-9): 657-665.

Honorati, M. C., M. Bovara, L. Cattini, A. Piacentini and A. Facchini (2002). "Contribution of interleukin 17 to human cartilage degradation and synovial inflammation in osteoarthritis." Osteoarthritis Cartilage 10(10): 799-807.

Hou, W. S., Z. Li, R. E. Gordon, K. Chan, M. J. Klein, R. Levy, M. Keysser, G. Keyszer and D. Bromme (2001). "Cathepsin k is a critical protease in synovial fibroblast-mediated collagen degradation." Am J Pathol 159(6): 2167-2177.

Huang, Z., C. Ding, T. Li and S. P. Yu (2018). "Current status and future prospects for disease modification in osteoarthritis." Rheumatology (Oxford) 57(suppl_4): iv108-iv123.

Hunter, D. J., J. Li, M. LaValley, D. C. Bauer, M. Nevitt, J. DeGroot, R. Poole, D. Eyre, A. Guermazi, D. Gale and D. T. Felson (2007). "Cartilage markers and their association with cartilage loss on magnetic resonance imaging in knee osteoarthritis: the Boston Osteoarthritis Knee Study." Arthritis Res Ther 9(5): R108.

Jahn, S. and J. Klein (2018). "Lubrication of articular cartilage." Physics Today 71(4): 48-54.

Karsdal, M. A., S. H. Madsen, C. Christiansen, K. Henriksen, A. J. Fosang and B. C. Sondergaard (2008). "Cartilage degradation is fully reversible in the presence of aggrecanase but not matrix metalloproteinase activity." Arthritis Res Ther 10(3): R63.

Kojima, T., F. Mwale, T. Yasuda, C. Girard, A. R. Poole and S. Laverty (2001). "Early degradation of type IX and type II collagen with the onset of experimental inflammatory arthritis." Arthritis Rheum 44(1): 120-127

Krueger, R. C., Jr., T. A. Fields, J. t. Hildreth and N. B. Schwartz (1990). "Chick cartilage chondroitin sulfate proteoglycan core protein. I. Generation and characterization of peptides and specificity for glycosaminoglycan attachment." J Biol Chem 265(20): 12075-12087.

Larsson, S., L. Lohmander and A. Struglics (2014). "An ARGS-aggrecan assay for analysis in blood and synovial fluid." Osteoarthritis and cartilage 22(2): 242-249.

Malemud, C. J. (2018). "Pharmacologic Interventions for Preventing Chondrocyte Apoptosis in Rheumatoid Arthritis and Osteoarthritis." Drug Discovery: Concepts to Market 45: 77.

Malemud, C. J. (2019). "Inhibition of MMPs and ADAM/ADAMTS." Biochem Pharmacol 165: 33-40.

Malfait, A. and M. Tortorella (2019). "The "elusive DMOAD": Aggrecanase inhibition from laboratory to clinic." Clin Exp Rheumatol 37(Suppl 120): S130-134.

Manicourt, D. H., M. Azria, L. Mindeholm, E. J. Thonar and J. P. Devogelaer (2006). "Oral salmon calcitonin reduces Lequesne's algofunctional index scores and decreases urinary and serum levels of biomarkers of joint metabolism in knee osteoarthritis." Arthritis Rheum 54(10): 3205-3211.

Martel-Pelletier, J., G. Tardif, J. Fernandes and J.-P. Pelletier (2000). Metalloproteases and their modulation as treatment in osteoarthritis, Totowa, NJ: Humana Press.

Mazieres, B., P. Garnero, A. Gueguen, M. Abbal, L. Berdah, M. Lequesne, M. Nguyen, J. P. Salles, E. Vignon and M. Dougados (2006). "Molecular markers of cartilage breakdown and synovitis at baseline as predictors of structural progression of hip osteoarthritis. The ECHODIAH Cohort." Ann Rheum Dis 65(3): 354-359.

Mohan, V., D. Talmi-Frank, V. Arkadash, N. Papo and I. Sagi (2016). "Matrix metalloproteinase protein inhibitors: highlighting a new beginning for metalloproteinases in medicine." Metalloproteinases in Medicine 3: 31.

Mullan, R. H., C. Matthews, B. Bresnihan, O. FitzGerald, L. King, A. R. Poole, U. Fearon and D. J. Veale (2007). "Early changes in serum type II collagen biomarkers predict radiographic progression at one year in inflammatory arthritis patients after biologic therapy." Arthritis Rheum 56(9): 2919-2928.

Nagase, H. and M. Kashiwagi (2003). "Aggrecanases and cartilage matrix degradation." Arthritis Res Ther 5(2): 94

Pelletier, J. P., J. Martel-Pelletier and S. B. Abramson (2001). "Osteoarthritis, an inflammatory disease: potential implication for the selection of new therapeutic targets." Arthritis Rheum 44(6): 1237-1247.

Pelletier, J. P., J. Martel-Pelletier and D. Howell (2000). Etiopathogenesis of osteoarthritis. Baltimore, Lippincott Williams & Wilkins.

Roach, H. I., N. Yamada, K. S. Cheung, S. Tilley, N. M. Clarke, R. O. Oreffo, S. Kokubun and F. Bronner (2005). "Association between the abnormal expression of matrix-degrading enzymes by human osteoarthritic chondrocytes and demethylation of specific CpG sites in the promoter regions." Arthritis Rheum 52(10): 3110-3124.

Schminke, B., S. Trautmann, B. Mai, N. Miosge and S. Blaschke (2016). "Interleukin 17 inhibits progenitor cells in rheumatoid arthritis cartilage." Eur J Immunol 46(2): 440-445.

Sharif, M., E. George, L. Shepstone, W. Knudson, E. J. Thonar, J. Cushnaghan and P. Dieppe (1995). "Serum hyaluronic acid level as a predictor of disease progression in osteoarthritis of the knee." Arthritis Rheum 38(6): 760-767.

Shin, J., K. B. Hosur, K. Pyaram, R. Jotwani, S. Liang, T. Chavakis and G. Hajishengallis (2013). "Expression and function of the homeostatic molecule Del-1 in endothelial cells and the periodontal tissue." Clinical and developmental immunology 2013.

Shiomi, T., V. Lemaitre, J. D'Armiento and Y. Okada (2010). "Matrix metalloproteinases, a disintegrin and metalloproteinases, and a disintegrin and metalloproteinases with thrombospondin motifs in non-neoplastic diseases." Pathol Int 60(7): 477-496.

Singh, P., K. B. Marcu, M. B. Goldring and M. Otero (2019). "Phenotypic instability of chondrocytes in osteoarthritis: on a path to hypertrophy." Annals of the New York Academy of Sciences 1442(1): 17-34.

Sorsa, T., T. Salo, E. Koivunen, J. Tyynelä, Y. T. Konttinen, U. Bergmann, A. Tuuttila, E. Niemi, O. Teronen and P. Heikkilä (1997). "Activation of type IV procollagenases by human tumor-associated trypsin-2." Journal of Biological Chemistry 272(34): 21067-21074.

Tervahartiala, T., T. Ingman, T. Sorsa, Y. Ding, P. Kangaspunta and Y. T. Konttinen (1995). "Proteolytic enzymes as indicators of periodontal health in gingival crevicular fluid of patients with Sjogren's syndrome." Eur J Oral Sci 103(1): 11-16.

Troeberg, L. and H. Nagase (2012). "Proteases involved in cartilage matrix degradation in osteoarthritis." Biochim Biophys Acta 1824(1): 133-145.

Wang, M., E. R. Sampson, H. Jin, J. Li, Q. H. Ke, H. J. Im and D. Chen (2013). "MMP13 is a critical target gene during the progression of osteoarthritis." Arthritis Res Ther 15(1): R5.

Wang, Z., T. Boyko, M. C. Tran, M. LaRussa, N. Bhatia, V. Rashidi, M. T. Longaker and G. P. Yang (2018). "DEL1 protects against chondrocyte apoptosis through integrin binding." J Surg Res. 231:1-9.(doi): 10.1016/j.jss.2018.1004.1066. Epub 2018 May 1030.

Wang, Z., M. C. Tran, N. J. Bhatia, A. W. Hsing, C. Chen, M. F. LaRussa, E. Fattakhov, V. Rashidi, K. Y. Jang, K. J. Choo, X. Nie, J. A. Mathy, M. T. Longaker, R. H. Dauskardt, J. A. Helms and G. P. Yang (2016). "Dell Knockout Mice Developed More Severe Osteoarthritis Associated with Increased Susceptibility of Chondrocytes to Apoptosis." PLoS One 11(8): e0160684.

Wells, A. F., L. Klareskog, S. Lindblad and T. C. Laurent (1992). "Correlation between increased hyaluronan localized in arthritic synovium and the presence of proliferating cells. A role for macrophage-derived factors." Arthritis Rheum 35(4): 391-396.

Verstappen, S. M., A. R. Poole, M. Ionescu, L. E. King, M. Abrahamowicz, D. M. Hofman, J. W. Bijlsma and F. P. Lafeber (2006). "Radiographic joint damage in rheumatoid arthritis is associated with differences in cartilage turnover and can be predicted by serum biomarkers: an evaluation from 1 to 4 years after diagnosis." Arthritis Res Ther 8(1): R31.

Vilen, S.-T., T. Salo, T. Sorsa and P. Nyberg (2013). "Fluctuating roles of matrix metalloproteinase-9 in oral squamous cell carcinoma." The Scientific World Journal 2013.

Vincenti, M. P. and C. E. Brinckerhoff (2002). "Transcriptional regulation of collagenase (MMP-1, MMP-13) genes in arthritis: integration of complex signaling pathways for the recruitment of gene-specific transcription factors." *Arthritis Res* 4(3): 157-164.

Yoshihara, Y., H. Nakamura, K. Obata, H. Yamada, T. Hayakawa, K. Fujikawa and Y. Okada (2000). "Matrix metalloproteinases and tissue inhibitors of metalloproteinases in synovial fluids from patients with rheumatoid arthritis or osteoarthritis." *Ann Rheum Dis* 59(6): 455-461.

The invention claimed is:

1. A method of prophylaxis and/or treating a disease or condition involving degradation of cartilage and/or disruption of cartilage homeostasis and/or integrity, the method comprising administering to a subject in need thereof a therapeutically effective amount of 2-Hydroxy-isocaproic acid (HICA), an enantiomer or a pharmaceutically acceptable salt thereof.

2. The method of claim 1, wherein the disease or condition is osteoarthritis or related degenerative and/or inflammatory conditions affecting joints.

3. The method of claim 1, wherein the disease is osteoarthritis or osteoarthritis including posttraumatic arthritis or a traumatic articular cartilage damage caused by any injury thereof.

4. The method of claim 1, wherein the method is by inhibiting ADAMTS and/or by inhibiting MMP-13 and/or by inhibiting fragmentation of DEL-1.

5. The method of claim 1, wherein the prophylaxis and/or treating a disease or condition involving degradation of cartilage and/or disruption of cartilage homeostasis and/or integrity comprises reducing pain, stiffness and aches of a joint, and thus resulting in asymptomatic joint.

6. A method of prophylaxis and/or treating a disease or condition involving degradation of cartilage and/or disruption of cartilage homeostasis and/or integrity, the method comprising administering to a subject in need thereof a therapeutically effective amount of a pharmaceutical composition comprising 2-hydroxy-isocaproic acid (HICA), an enantiomer or a pharmaceutically acceptable salt thereof, and one or more pharmaceutically acceptable carrier.

7. The method of claim 6, wherein the disease or condition is osteoarthritis or related degenerative and/or inflammatory condition affecting joints.

8. The method of claim 6, wherein the method further comprises administration of an additional therapeutic agent.

9. The method of claim 1, wherein the 2-Hydroxy-isocaproic acid (HICA), an enantiomer or a physiologically acceptable salt thereof is administered to the subject in an amount of 5-100 mg/kg/day.

* * * * *